United States Patent [19]
Beaver

[11] Patent Number: 5,830,442
[45] Date of Patent: Nov. 3, 1998

[54] PIGMENTED ARTIFICIAL ACRYLIC FINGERNAIL

[76] Inventor: Janet K. Beaver, 303 W. Wallace, San Saba, Tex. 76877

[21] Appl. No.: 763,114

[22] Filed: Dec. 10, 1996

Related U.S. Application Data

[63] Continuation-in-part of Ser. No. 353,283, Dec. 5, 1994, abandoned, which is a continuation-in-part of Ser. No. 75,384, Jun. 14, 1993, abandoned.

[51] Int. Cl.$^6$ .................................................. A61K 7/043
[52] U.S. Cl. ............................................. 424/61; 424/63
[58] Field of Search ......................................... 424/61, 63

[56] References Cited

U.S. PATENT DOCUMENTS

| | | | |
|---|---|---|---|
| 3,864,294 | 2/1975 | Busch, Jr. | 260/285 N |
| 4,058,442 | 11/1977 | Lee, Jr. et al. | 204/159.12 |
| 4,104,333 | 8/1978 | Lee, Jr. et al. | 260/885 |
| 4,224,451 | 9/1980 | Roberts et al. | 548/260 |
| 4,229,431 | 10/1980 | Lee, Jr. et al. | 424/61 |
| 4,260,701 | 4/1981 | Lee, Jr. | 525/303 |
| 4,708,866 | 11/1987 | Turco et al. | 424/61 |
| 5,133,966 | 7/1992 | Khamis | 424/401 |

OTHER PUBLICATIONS

Harry, Ralph Gordon, F.R.I.C., F.R.S.M., A.R.P.S., Harry's Cosmeticology, *The Principles and Practice of Modern Cosmetics*, vol. One, pp. 203 & 204.

Owens, Barbara A., Nail Color—Then Now, NAILPRO, Jan. 1996, pp. 47,50–51,61.

*Primary Examiner*—Jyothsna Venkat
*Attorney, Agent, or Firm*—Evan M. Kent, Esq.; Russ, August & Kabat

[57] ABSTRACT

An artificial nail is made from a liquid methacrylate monomer, a powdered acrylic or methacrylate polymer, and a catalyst including an activator and an accelerator. A pigment is mixed with the powder so the resultant nail has the glossy, opaque appearance expected from a conventionally applied nail polish. The pigment is present in the range of 1.5–15% by weight of the powder and exhibits a color having a wavelength of 4000–7000 Angstroms.

46 Claims, No Drawings

PIGMENTED ARTIFICIAL ACRYLIC FINGERNAIL

This application is a continuation-in-part of application Ser. No. 08/353,283, filed Dec. 5, 1994 now abandoned which is a CIP of Ser. No. 08/075,384, filed Jun. 14, 1993, now abandoned.

BACKGROUND OF THE INVENTION

This invention relates to a pigmented artificial fingernail and more particularly to an artificial fingernail having the appearance of being coated with a glossy opaque nail polish caused by a pigment dispersed throughout the artificial nail.

Artificial fingernails are commonly applied by nail technicians and are of four generally commercially available types: acrylic based nails, gel nails, rigid artificial nails and wraps. Gel nails are polymerized by the application of violet and ultraviolet light and have not been as well received as acrylic based nails for a variety of reasons. Rigid artificial nails are glued to the existing nail of the user. Wraps include fiberglass or silk that are glued to a tip or to an existing nail. This invention is limited to acrylic based nails of the type that are polymerized by mixing a monomer with a catalyst and then by applying the mixture to the nail of the wearer.

The most popular and widely-used artificial fingernail compositions have been two part (usually liquid and powder) formulations where a liquid portion usually consists of a methacrylate monomer and a small amount of a polymerization accelerator or promoter, such as a tertiary amine, and a powder portion generally consists of polymethyl methacrylate and a catalyst, such as benzoyl peroxide. In general, the chemistry of acrylic and methacrylic acid polymers is well known in the art as shown in the Encyclopedia of Polymer Science and Engineering, Volume 1, Second Edition, pp 211 et seq., Kirk-Othmer: Encyclopedia of Chemical Technology, Volume 1, Third Edition, pp 330 et seq., which are incorporated herein by reference.

In situ polymerization is accomplished by mixing a small amount of the liquid with a small amount of the powder. With commercially acceptable materials, the catalysts have been selected so mixing is done either on the end of a brush, on the nail of the wearer or a combination thereof. It is possible, of course, for the polymerization reaction to be slow enough that mixing could be done in a separate container. Typically, a brush is dipped into the liquid, some of the liquid is wiped off on the edge of the liquid container and the brush is then dipped into the powder. This creates a ball of product on the end of the brush which is then brushed on the natural nail surface to be repaired, protected or elongated.

Elongation of the nail surface beyond the end of the natural nail is done in one of two ways. In a full sculpting technique, a substrate having the general contour of the natural nail is placed under the surface of the natural nail. The substrate is of a material which does not adhere to the polymerizable mixture. After construction of the artificial nail, the substrate is removed.

In a tip overlay method, a rigid plastic tip is glued to the natural nail. Conventional tips have a ridge on the underside to abut the end of the natural nail so the tip extends well beyond the end of the natural nail and extends part way toward the cuticle, usually about one third or one half of the length of the natural nail. The polymerizable material is applied to the tip in the same general manner as in the full sculpting procedure so the artificial nail covers the tip and the natural nail. As will be apparent hereinafter, the technique of this invention is usable in the full sculpting technique, natural nail overlay, or in the tip overlay procedure. The procedure selected is a matter of preference of the nail technician.

In the tip overlay procedure, it is preferred that the consistency of the polymerizable material vary in response to the location to which it is applied. Material applied to the tip itself and to the exposed junction between the tip and the natural nail preferably has a greater proportion of powder than material applied near the cuticle. Thus, the material applied to the tip and to the junction is thicker while the material applied near the junction of the natural nail and the cuticle is less viscous. This allows the thinner material to conform to the shape of the cuticle.

Blending the powder/liquid portions, as by dipping the brush in the liquid and then in the powder and then brushing on the nail or tip overlay, results in the powder dissolving in the liquid monomer, and the monomer polymerizing through the action of the accelerator and catalyst. The mixing and brushing steps are repeated as often as needed to create a nail of the desired length, thickness and shape. Using the prior materials, when the prior art artificial nail is large enough, it may be smoothed, shaped and a nail polish applied if desired. In the case of a tip overlay, the tip is usually much longer than the desired length of the artificial nail so the tip is trimmed off or cut to length.

One of the difficulties with prior art artificial nails lies in polishing the nail. Persons who apply artificial nails are known as nail technicians. Nail technicians can hardly wear conventional polished artificial nails because the nail polish remover used to remove polish from customers' nails also removes polish from the nail technician's nails. Thus, every time a nail technician works on a set of polished prior art nails, the nail technician has to repolish her own nails. There are many other situations where the application of nail polish to an artificial nail is unsatisfactory or undesirable, such as typists or other professions requiring extensive use of the hands where chipping is likely. Many wearers of artificial nails would enjoy having a permanently polished artificial nail that does not require periodic repair or repolishing.

Typical disclosures of self polymerizing methacrylate artificial nails that include very small amounts of pigment are found in U.S. Pat. Nos. 4,104,333; 4,229,431; 4,260,701 and 4,708,866. These pigments, however, are limited to extremely small amounts or in the case of $TiO_2$ to provide a white tip for providing a natural nail look.

Other disclosures of methacrylate polymer artificial nails are found in U.S. Pat. Nos. 3,750,684; 3,786,821; 4,058,442; 4,361,160; 4,405,750; 4,407,310; 4,408,622; 4,495,172; 4,596,260; 4,615,348; 4,626,428; 4,669,491; 4,682,612; 4,687,827; 4,690,369; 4,704,303; 4,718,957; 4,780,512; 4,860,774; 4,871,534; 5,093,108; 5,098,696; 5,115,495; 5,127,414 and 5,206,011. The disclosures of these patents are incorporated herein by reference.

In its broadest aspect, this invention comprises mixing pigment with one or both of the components of a self polymerizing acrylic artificial nail to produce an artificial nail having a dispersed pigment therein providing a glossy, opaque appearance comparable to an artificial nail to which a red or reddish nail polish has been applied. Such a nail will remain polished in appearance even though the wearer handles nail polish remover which would remove or partially remove conventional nail polish. If it is desired to do so, a conventional nail polish may be applied to the colored artificial nail of this invention to change the color of the nail.

Conventional nail polish remover will remove the nail polish but leave the underlying pigmented nail untouched.

Those skilled in the art object to the concept of making artificial nails with a dispersed opaque pigment having the appearance of a glossy, polished nail because of the problems with fungi or green spot. Wearers of conventional artificial nails often develop a condition known as green spot or mildew between the artificial nail and the natural nail. Green spot is caused by the artificial nail pulling away from the natural nail. Moisture is then trapped causing bacteria or fungi to grow between the nails. More serious fungi infections develop in much the same manner and are more severe because the growing organism is more persistent and tends to infect the underlying natural nail.

Green spot and fungi infections are controllable in prior art artificial nails because they are seen when the nail polish is stripped off. The nail polish might be stripped off by the wearer when repolishing the artificial nails. The nail polish is also stripped off by a nail technician when repairing a nail or when "filling in". Filling in occurs when the natural nail has grown out and the gap between the end of the artificial nail and the cuticle becomes objectionable. In this procedure, the nail technician applies new polymer to the gap, allows it to harden and then buffs it until it merges smoothly with the old artificial nail. After applying new nail polish, the old nail looks new again. The process is repeated every few weeks when the nail grows out provided the nail adheres to the underlying natural nail. Any green spot or fungi infection is apparent when the polish is removed from the prior art nail. If any appears, the artificial nail is removed and the infection is treated.

Filling in the gap between the artificial nail and the cuticle has been thought to be highly desirable in prior practice and, in fact, is the standard of the industry. It is appealing for several reasons. First, one of the problems with artificial nails is they periodically come loose from the underlying natural nail and have to be replaced. This is inconvenient to the customer and time consuming to the nail technician. Second, it is much preferred by the profession to fill in the gap rather than replace the nail because it is quicker for the nail technician to fill in the gap between the old nail and the cuticle than to remove the nail and start anew. Third, filling in has been done for a long time and nail technicians, like other people, are reluctant to change.

In this invention, no filling in is done or, at most, one or two fill ins are done. When the natural nail has grown out enough to produce an objectionable gap between the artificial nail and the cuticle, the old nail may then be filled in or removed and a new one applied over the natural nail thus providing a much more durable and secure nail since freshly applied acrylic has not begun to get brittle or loose. The old artificial nail must be removed periodically, the natural nail is examined and any evidence of green spot or fungus infection is seen and treated.

The prior art is divided into several categories. One group comprises preformed rigid artificial nails that are glued onto the natural nail of the wearer. Preformed artificial nails in this group are worn for a very short time, for example one evening, and then removed because they do not adhere well to the underlying nail and do not have the longevity or durability of so called sculptured nails which are applied as a liquid or paste to the wearer's nails and then polymerized to provide a hard, tough artificial nail that adheres to the natural nail for an acceptable period. Many preformed artificial nails are permanently colored by the incorporation of pigment therein. A wide selection of colors is normally available because they are limited to very short term use because of the inherent adhesion problems. These type nails might be used to change one's appearance for a single particularly important social event.

A second group of artificial nails are so called gel nails which are brushed onto the underlying nail of the wearer and then polymerized by the application of violet or ultraviolet light. Nails of this group are either transparent, colored slightly to appear naturally colored or are colored sufficiently to be an opaque red. Indications are that when filling in is done with the heavily colored gel nails, they appear transparent around the cuticle.

A third group of artificial nails are known as wraps and include gluing layers of fiberglass or silk on a tip or on the wearer's existing nail.

A fourth group of artificial nails are catalyzed methacrylates in which a liquid and powder are mixed and then applied to the nails. Artificial nails of this group are either unpigmented or slightly pigmented to provide naturally appearing nail having an unpolished appearance. The amount of pigment in these prior art nails is very small as shown in U.S. Pat. Nos. 4,104,333; 4,229,431; 4,260,701 and 4,708,866. The only nail created is an unpolished, translucent looking nail.

SUMMARY OF THE INVENTION

It is an object of this invention to provide an artificial nail having a pigment dispersed therein providing an opaque, glossy finish comparable to a nail covered with a nail polish.

Another object of this invention is to provide an artificial nail having a sufficient amount of a predetermined colored pigment dispersed therein to provide a finished nail product having the predetermined color which does not need to have polish applied.

Still another objection of the invention is to provide a composition for forming an artificial nail including a liquid component comprising about 10–98% of a lower alkylmethacrylate monomer and from about 0.1–5% of a polymerization accelerator and a powder component comprising from about 50–95% of a lower alkylmethacrylate polymer and an acrylic ester polymer, from about 0.1–5% of a polymerization initiator and from about 1.5–15% of a pigment by weight of the powder or 0.4%–10% of total composition, dispersed throughout the polymer. The pigment is sufficient to impart a colored, opaque finish to the nail.

It has been discovered that the object of providing an opaque glossy acrylic fingernail can be accomplished with a much smaller proportion of pigment than previously realized. Indeed, darker colors can be accomplished by a relatively small amount of pigment. Lighter colors can be typically produced by diluting the pigment with a white pigment, such as titanium dioxide. Pearlized colors may also be provided by adding an effective amount of pearlized pigment.

In another aspect, this invention comprises a method of applying an artificial nail to a natural nail of a person, comprising mixing a liquid methacrylate monomer, a powder selected from the group comprising methacrylate polymers, acrylic ester polymers, a catalyst and a pigment, the pigment being at least 1.5% by weight of the powder, or 0.4% of the total composition, and exhibiting a wavelength of anywhere from 4000–7000 Angstroms, and applying the mixture to the natural nail and/or extension and allowing the mixture to polymerize into an artificial nail having a glossy, opaque finish. Consequently, the pigment may be any color in the visible spectrum from violet to red. Such a colored pigment is sufficient to impart a colored, opaque finish to the nail, which does not require a subsequent application of nail polish.

These and other objects of this invention will become more fully apparent as this description proceeds, reference being made to the accompanying drawings and appended claims.

Although this invention has been disclosed and described in its preferred forms with a certain degree of particularity, it is understood that the present disclosure of the preferred forms is only by way of example and that numerous changes in the details of construction and operation and in the combination and arrangement of parts may be resorted to without departing from the spirit and scope of the invention as hereinafter claimed.

DETAILED DESCRIPTION OF THE INVENTION

The foregoing objects and others are accomplished in this invention by incorporating an sufficient quantity of a pigment in one or both of the components of a catalyzed methacrylate type artificial nail. The composition of this invention comprises an alkylmethacrylate monomer, an alkylmethacrylate polymer, a peroxide catalyst, an accelerator and a pigment The pigment is used in a large enough quantity to provide the opacity and color of the finished nail. The gloss or sheen of the finished nail is caused more by the methacrylate polymer and the degree to which it is buffed than by the pigment.

Normally, the present composition involves the use of a liquid and a powder. The liquid contains a lower alkylmethacrylate monomer. Methylmethacrylate was originally widely used for artificial fingernail compositions until it was determined that the adjacent alkylmethacrylate monomers, such as ethylmethacrylate, butylmethacrylate and propylmethacrylate were less toxic and promoted allergies to a lesser extent and were thus more desirable. The powder contains a polymerized lower alkylmethacrylate such as polymethylmethacrylate and/or an acrylic ester polymer. The powder contains a polymerization initiator or catalyst such as peroxide which causes the composition to cure in-situ on the surface of the natural nail. Any suitable initiator such as lauroyl peroxide or benzoyl peroxide may be used. Any suitable accelerator such as tertiary aromatic amine and such as those disclosed in U.S. Pat. No. 4,495,172 may also be used in this invention and is normally a part of the liquid component. The technique used to mix and polymerize the components of this invention is as disclosed in the above cited U.S. Patents and in the *Encyclopedia of Polymer Science and Technology*, John Wiley and Sons, Inc. volume 1, pp 263–97 (1964), which is incorporated by reference into this disclosure.

The ability of the initiator to cure the nail coating composition may be enhanced through the use of activators or accelerators. Thus, a peroxide initiator can be activated with a tertiary aromatic amine such as an N,N-di(lower)alkyl-p-toluidine e.g., N,N-dimethyl-p-toluidine, N,N-diethyl-p-toluidine and especially N,N bis(2-hydroxyethyl-p-toluidine).

The various components of the nail coating compositions may be combined in any suitable manner, and any of the compositions of the above prior art patents may be used together with a sufficient amount of pigments in accordance with this invention. However, because chemically initiated polymerization starts immediately upon a mixture of all three of (1) methacrylate monomers, (2) an initiator and (3) an activator, it is necessary to separate at least one of these components from the others until immediately before the application of the nail coating to human nails. This separation may be achieved through the use of a two-package product, wherein various components of the nail composition are separately contained until the time of application to nails. As will be more fully apparent hereinafter, a liquid component preferably contains a liquid monomer and the accelerator while a powder component contains the polymer and the peroxide.

The monomers used in this invention are methylmethacrylate, ethylmethacrylate, butylmethacrylate, propylmethacrylate and mixtures thereof. The monomer presently preferred by professional nail technicians is known to have a quite noticeable odor. Low odor or odorless monomers have been proposed to the trade but are not yet well received. This invention is usable with any methacrylate monomer. The polymerizable acrylic ester monomers used in this invention are selected from methylacrylic esters, ethylacrylic esters, butylacrylic esters and mixtures thereof. These acrylic esters preferably have a polymeric filler dissolved therein.

In the preferred embodiments of this invention, a sufficient amount of pigment is added to the formation comprising ethylmethacrylate monomer, methylmethacrylate polymer, benzoyl peroxide and an accelerator, i.e. the powder. The pigment may be a red or reddish color by which is meant that light reflected off the pigment has a wavelength in the range of 5700–7000 Angstroms. Other colors, however, are equally applicable to the present invention to provide a wide variety of possible predetermined colors, such as violet, blue, green, yellow, etc. Therefore, the pigment useful in the present invention may reflect light at any wavelength in the range of 4000–7000 Angstroms.

The pigment is preferably thoroughly mixed with the powdered methacrylate polymer during or before packaging so the powder that is ultimately mixed with the liquid already contains the pigment. As a result, the pigment should have a particle size similar to that of the powdered methacrylate polymer. The pigment is generally ground or comminuted. The pigment may be ground to a size range of 0.5–1 microns, however, any suitable particle size may be used.

The pigment of the present invention is mixed, during an initial stage, with the powder component of the nail formulation for more even distribution throughout the resultant composition. The selected pigments are not soluble in the monomers of the present liquid component, and thus would not provide for even mixing throughout the resultant composition. Conventional dyes, on the other hand, are soluble in monomers.

The pigment may be of any suitable type, such as lead chromates, organic pigments, cadmium based pigments or pearlescent or iridescent pigments. The preferred pigments are organic red pigments available from Sun Chemical, 4526 Chickering Avenue, Cincinnati, Ohio 45232 and Warner Jenkinson, 107 Wade Avenue, South Plainfield, N.J. 07080. Many other color pigments are possible, however, to provide the desired resulting color.

The pigment is preferably added to the powder in the range of about 1.5–15% by weight of the powder. The exact amount of the pigment that is incorporated in the resultant artificial nail will determine the ratio of liquid to powder applied by the nail technician. With too little pigment, the resultant nail does not have the opaque, colored appearance of a nail covered with a conventional nail polish. In this invention, the opacity and color is provided by the pigment but the gloss is largely a function of the methacrylate polymer in which the pigment is dispersed.

The compositions of this invention may also contain such additives as antioxidants, calcium compounds to promote hardening of the natural nail, conventional solvent type plasticizers such as phthalate esters, opacifiers or colorant extenders such as titanium dioxide or alkyl polysiloxane, and conventional dispersing agents for pigments and the like.

Lighter shades of color, such as red, can be formed by adding a relatively large amount of white opacifier, usually titanium dioxide, to the powder. The titanium dioxide effectively dilutes the pigment to provide a lighter color.

Pearlized colors are provided by adding pearlescent or iridescent pigments in a relatively large amount, relative to the chosen colored pigment. Pearlescent pigments are available in a wide variety of colors from Mearl Corporation, New York, N.Y.

The use of pigments in the present invention is preferred, over dyes for example, because pigments provide for a much more intense coloration, whereas dyes typically only provide for tinting or shading.

The nail of this invention is made by removing any existing artificial nail, pushing back the cuticle, buffing the natural shine from the nail, gluing the tip overlays on the natural nail, clipping off the tip overlays, buffing the shine off the tip overlays and buffing down the ridges of the overlays, spraying the nails and overlays with a nail cleanser, applying a primer, mixing the powder and liquid and applying the mixture to the natural human nail and/or extensions.

The preferred technique is to create a ball of product on the end of a brush of the size used by artists and apply the ball to the tip of the substrate or tip overlay, brushing the material toward the tip. Additional balls of material are then applied inwardly toward the cuticle and brushed toward the tip. The ball of product applied near the cuticle is preferably thinner and less viscous, i.e. it contains less powder, than the material applied near the tip. Surprisingly, the color of the nail near the tip is the same as the nail near the cuticle even though there is necessarily more pigment near the tip.

The mixture is brushed over the natural nail and any substrate or tip overlay acting as an extender. The technician adds material until the nail has reached the desired thickness, length and overall shape. The nail cures to a colored velvety finish in about a minute. After the nail cures, the technician files and shapes the nail in a conventional manner. By buffing with a conventional hand held buffer and some oil, the resultant nail is glossy and colored with the appearance of a conventional artificial nail covered with a conventional nail polish.

The curing mechanism of the present invention is specifically tailored to accommodate the use of pigment. Pigments reflect visible light, thus providing coloration. They also are capable of absorbing and reflecting ultraviolet radiation. Therefore, incorporating colored pigment into photo-curable systems results in a dramatic lowering of the cure efficiency, significantly reducing the physical properties of a cured artificial nail. Dyes on the other hand, such as those disclosed in U.S. Pat. No. 4,058,442, are perfectly suited for UV cure systems, because dyes do not absorb UV light.

The artificial nail of this invention may be maintained or repaired in any conventional manner because the properties of the nail, except color and opacity, are that of the polymerized methacrylate. When the natural nail first grows out to provide a noticeable gap between the nail and the cuticle, the technician or user buffs the ridge of the artificial nail near the cuticle and applies a coat of conventional nail polish. Because the underlying nail is colored, only one coat of polish is necessary, in contrast to conventional unpigmented artificial nails which require up to four coats of conventional polish.

Sooner or later, the nail grows out to an extent where a conventional artificial nail would be filled in. In this invention, there is preferably no filling in, however, 1 or 2 fill ins may be done. Upon removal, the nail technician removes the old nail, inspects for green spot or fungi infections and, if none, applies a new artificial nail of this invention. The full sculpt, natural nail overlay or tip overlay procedure can be used depending on the preference of the nail tech.

EXAMPLES

The composition of the present invention will be more fully described by reference to the following examples. Parts are by weight unless specified to the contrary. The Creative Nail Design CONTOURS™ odor materials disclosed below are commercially available artificial nail materials available from Creative Nail Design, Inc. of Carlsbad, Calif. Each of the following examples are generally used by the following method. Namely, the liquid and powder were mixed in 2½–3 parts liquid to 1 part powder by dipping a brush in the liquid and then dipping the brush in the powder and applying it to the nails, unless otherwise stated. The resultant nail was a hard, tough, long lasting adhering artificial nail having an opaque, glossy appearance comparable to a prior art artificial nail which had been polished with a conventional nail polish.

Example I

A nail composition is formulated as follows:

|  | Percent |
| --- | --- |
| Liquid | |
| Creative Nail Design CONTOURS ™ liquid | 100% |
| Powder | |
| Creative Nail Design CONTOURS ™ clear powder | 85% |
| SCM Cadnium Pure Red Medium #4560 pigment | 15% |

Example II

A nail composition is formulated as follows:

|  | Percent |
| --- | --- |
| Liquid | |
| Creative Nail Design CONTOURS ™ liquid | 100% |
| Powder | |
| Creative Nail Design CONTOURS ™ clear powder | 90% |
| SCM Cadnium Pure Red Medium #4570 pigment | 10% |

Example III

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 95% |
| SCM Cadnium Pure Red Medium #4590 pigment | 5% |

Example IV

A nail composition is formulated as follows:

| Ingredient | Percent |
|---|---|
| methylmethacrylate monomer | 35% |
| methylmethacrylate polymer | 35% |
| acrylic ester polymer | 15% |
| benzoyl peroxide | 3% |
| SCM Cadnium Pure Red Maroon #4590 | 10% |
| accelerator | 2% |

Example V

A nail composition is formulated as follows:

| Ingredient | Percent |
|---|---|
| methylmethacrylate monomer | 40% |
| copolymer of ethyl and methylmethacrylate | 35% |
| benzoyl peroxide | 3% |
| SCM Cadnium Pure Red Light #4540 | 8% |
| titanium dioxide | 1% |
| calcium carbonate | 10% |
| accelerator | 3% |

Example VI

A nail composition is formulated as follows:

| | Percent |
|---|---|
| Liquid | |
| ethoxyethyl methacrylate | 95% |
| diethyleneglycol dimethacrylate | 2% |
| dimethacrylate N,N bis(2-hydroxyethyl-p-toluidine | 2.9% |
| BHT (antioxidant) | 0.1% |
| Powder | |
| polyethyl methacrylate | 88% |
| benzoyl peroxide | 2% |
| SCM Cadnium Pure Orange Deep #4520 pigment | 10% |

Example VII

A nail composition is formulated as follows:

| Ingredient | Percent |
|---|---|
| methylmethacrylate monomer | 40% |
| methylmethacrylate polymer | 25% |
| acrylic ester polymer | 15% |
| calcium carbonate | 8% |
| benzoyl peroxide | 2% |
| titanium dioxide | 4% |
| SCM Cadnium Pure Red Medium #4560 | 4% |
| accelerator | 2% |

Example VIII

A nail composition is formulated as follows:

| Ingredient | Percent |
|---|---|
| methylmethacrylate monomer | 30% |
| mixture of methacrylic acid and isobutyl methacrylate | 10% |
| copolymer of ethyl and methyl methacrylate polymer | 25% |
| methylmethacrylate polymer | 20% |
| benzoyl peroxide | 3% |
| titanium dioxide | 5% |
| SCM Cadnium Pure Orange Medium #4510 | 5% |
| accelerator | 2% |

Example IX (Color #101)

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 96.3% |
| Pigment: DC#7C19-003; DC#6C19-0112; DC#6C19-6619 $TiO_2$ | 3.7% |

Example X (Color #102)

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 96.29% |
| Pigment: | 3.13% |
| $TiO_2$ | .58% |

Example X (Color #103)

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 92.5% |
| Pigment: DC#6C19012; DC#6C196619; DC#5C694424; Russett C338075; MP45, MP1001 pearlescent pigment; $TiO_2$ | 7.5% |

Example XI (Color #104)

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 97.0% |
| Pigment: Russett C338075; DC#7C19003 pigment; $TiO_2$ | 3.0% |

Example XII (Color #105)

A nail composition is formulated as follows:

| | Percent |
|---|---|
| Liquid | |
| ethoxyethyl methacrylate | 95% |
| diethyleneglycol dimethacrylate | 2% |
| dimethacrylate N,N bis(2-hydroxyethyl)-p-toluidine | 2.9% |
| BHT (antioxidant) | .1% |
| Powder | |
| polyethyl methacrylate | 96.5% |
| benzoyl peroxide | 2% |
| D&C7C19003, DC34-C24012 pigment | 1.5% |

The liquid and powder were mixed at a weight ratio of about 1.2 liquid to powder.

Example XIII (Color #106)

A nail composition is formulated as follows:

| Ingredient | Percent |
|---|---|
| ethylmethacrylate monomer | 38.5% |
| methylmethacrylate polymer | 38.5% |
| acrylic ester polymer | 15% |
| benzoyl peroxide | 3% |
| accelerator | 2% |
| Pigment: DC6C19012; DC6C196619; $TiO_2$ | 3.0% |

Example XI (Color #107)

A nail composition is formulated as follows:

| | Percent |
|---|---|
| Liquid | |
| Creative Nail Design CONTOURS ™ liquid | 100% |
| Powder | |
| Creative Nail Design CONTOURS ™ clear powder | 97.06% |
| Pigment: | .43% |
| $TiO_2$ | 2.51% |

Example XIV (Color #108)

A nail composition is formulated as follows:

| Ingredient | Percent |
|---|---|
| ethylmethacrylate monomer | 42% |
| copolymer of ethyl and methylmethacrylate | 37.8% |
| benzoyl peroxide | 3% |
| calcium carbonate | 10% |
| accelerator | 3% |
| Pigment: DC34-C24012, DC7-C19003; $TiO_2$; MP1005, MP45, MP1001 pearlescent pigment | 4.19% |

Example XV (Color #113)

A nail composition is formulated as follows:

| | Percent |
|---|---|
| Liquid | |
| ethoxyethyl methacrylate | 95% |
| diethyleneglycol dimethacrylate | 2% |
| dimethacrylate N,N bis(2-hydroxyethyl)-p-toluidine | 2.9% |
| BHT (antioxidant) | .1% |
| Powder | |
| polyethyl methacrylate | 95.1% |
| benzoyl peroxide | 2% |
| Pigment: DC7-C19003; DC34-C24012; DC6-C196619; $TiO_2$; Super Gold W215117 pearlescent pigment | 2.9% |

The liquid and powder were mixed at a weight ratio of about 1.2 liquid to powder.

Example XVI (Color #114)

A nail composition is formulated as follows:

| Ingredient | Percent |
| --- | --- |
| ethyl methacrylate monomer | 37.4% |
| methyl methacrylate polymer | 25% |
| acrylic ester polymer | 15% |
| calcium carbonate | 8% |
| benzoyl peroxide | 2% |
| accelerator | 2% |
| Pigment: DC6C19012; DC34C24012; DC7C19003; $TiO_2$; MP45, Dichroma RB017191, MP1005 pearlescent pigment | 6.6% |

Example XVII (Color #115)

A nail composition is formulated as follows:

| Ingredient | Percent |
| --- | --- |
| ethylmethacrylate monomer | 32.2% |
| mixture of methacrylic acid and isobutyl methacrylate | 10% |
| copolymer of ethyl and methyl methacrylate polymer | 28% |
| methylmethacrylate polymer | 23% |
| benzoyl peroxide | 3% |
| Pigment: DC7-C19003; DC6-C19012; DC6-C196619; $TiO_2$ | 3.8% |
| accelerator | 2% |

Example XVIII (Color #116)

A nail composition is formulated as follows:

| | Percent |
| --- | --- |
| Liquid | |
| Creative Nail Design CONTOURS ™ liquid | 100% |
| Powder | |
| Creative Nail Design CONTOURS ™ clear powder | 98.2% |
| Pigment: DC34C24012; DC7C19003; $TiO_2$ | 1.8% |

Example XIX (Color #117)

A nail composition is formulated as follows:

| | Percent |
| --- | --- |
| Liquid | |
| Creative Nail Design CONTOURS ™ liquid | 100% |
| Powder | |
| Creative Nail Design CONTOURS ™ clear powder | 93.5% |
| Pigment: DC7C19003; Russett C338075; DC34C24012; $TiO_2$; Super Gold 017217, Coloronao Bronze 017353 pearlescent pigment | 6.5% |

Other ingredients may be added to the formulation of this invention to enhance or otherwise add to the beneficial effects of the invention. The preferred and optimum embodiments of the present invention have been described herein to illustrate the underlying principles of this invention, but it is to be understood that numerous modifications and ramifications may be made without departing from the spirit and scope of this invention.

Example XII (Color #118)

A nail composition is formulated as follows:

| | Percent |
| --- | --- |
| Liquid | |
| Creative Nail Design CONTOURS ™ liquid | 100% |
| Powder | |
| Creative Nail Design CONTOURS ™ clear powder | 93.26% |
| Pigment: | 6.16% |
| $TiO_2$ | .58% |

I claim:

1. A method for producing a self-curing, dermatologically-acceptable pigmented artificial nail composition, applied to a natural nail or nail extension, comprising the step of:
    mixing a powder component comprising:
        an alkylmethacrylate polymer;
        a polymerization initiator; and
        a pigment, said pigment is selected from the group consisting of lead chromate pigments, organic pigments, cadmium based pigments, pearlescent pigments, and mixtures thereof; with
    a liquid component comprising an alkylmethacrylate monomer;
    wherein said pigmented artificial nail composition hardens to form an evenly-colored glossy, opaque artificial nail, wherein said pigment is dispersed in said nail composition to provide a finished nail product.

2. The method as recited in claim 1, wherein said alkylmethacrylate polymer is polymethylmethacrylate.

3. The method as recited in claim 1, wherein said alkylmethacrylate monomer constitutes 10–98 weight percent of said liquid component.

4. The method as recited in claim 1, wherein said polymerization initiator constitutes 0.1–5.0 weight percent of said powder component.

5. The method as recited in claim 1, wherein said polymerization initiator is selected from the group consisting of peroxide, lauroyl peroxide, benzoyl peroxide and mixtures thereof.

6. The method as recited in claim 1, wherein said pigment constitutes 0.4–10.0 weight percent of said composition.

7. The method as recited in claim 1, wherein said pigment constitutes 1.5–15.0 weight percent of said powder component.

8. The method as recited in claim 1, wherein said pigment has a particle size of less than 5.0 microns.

9. The method as recited in claim 1, wherein said pigment exhibits a color selected from the group consisting of red, orange yellow, blue, indigo, violet and mixtures thereof.

10. The method as recited in claim 1, wherein said pigment exhibits a color having a wavelength in the range of 4000–7000 Angstroms.

11. The method as recited in claim 1, wherein said pigment exhibits a color having a wavelength in the range of 5700–7000 Angstroms.

12. The method as recited in claim 1, said powder component including a polymerizable acrylic ester monomer.

13. The method an recited in claim 12, wherein said polymerizable acrylic ester monomer is selected from the group consisting of methylacrylic esters, ethylacrylic esters, butylacrylic esters and mixtures thereof.

14. The method as recited in claim 12, wherein said alkylmethacrylate polymer and said polymerizable acrylic ester constitute 50–95 weight percent of said powder component.

15. The method as recited in claim 12, said polymerizable acrylic ester monomer further comprising a polymeric filler dissolved therein.

16. The method as recited in claim 1, wherein said alkylmethacrylate monomer of said liquid component is selected from the group consisting of ethylmethacrylate, butylmethacrylate, propylmethacrylate and mixtures thereof.

17. The method as recited in claim 1, including the step of mixing an accelerator with said powder component and said liquid component.

18. The method as recited in claim 17, wherein said accelerator is a tertiary aromatic amine.

19. The method as recited in claim 18, wherein said tertiary aromatic amine is selected from the group consisting of N,N-dimethyl-p-toluidine, N,N-diethyl-p-toluidine, N,N-bis(2-hydroxyethyl-p-toluidine) and mixtures thereof.

20. The method as recited in claim 1, wherein said composition further comprises an additive selected from the group consisting of antioxidants, hardeners, plasticizers, opacifiers, colorant extenders, dispersing agents for pigments and mixtures thereof.

21. The method as recited in claim 20, wherein said hardener is a calcium compound.

22. The method as recited in claim 20, wherein said plasticizer is a phthalate ester.

23. The method as recited in claim 20, wherein said colorant extender is selected from the group consisting of titanium dioxide, alkyl polysiloxane and mixtures thereof.

24. A self-curing, dermatologically acceptable composition applied to a natural nail or extension as a coating that hardened to form on evenly colored, glossy, opaque artificial nail comprising a powder component comprising:
   an alkylmethacrylate polymer;
   a polymerization initiator; and
   a pigment, said pigment is selected from the group consisting of lead chromate pigments, organic pigments, cadmium based pigments, pearlescent pigments, mixtures thereof; and
   a liquid component comprising an alkylmethacrylate.

25. The composition as recited in claim 24, wherein said aklylmethacrylate polymer polymethylmethacrylate.

26. The composition as recited in claim 24, wherein said alkylmethacrylate monomer constitutes 10–98 weight percent of said liquid component.

27. The composition as recited in claim 24, wherein said polymerization initiator constitutes 0.1–5.0 weight percent of said powder component.

28. The composition as recited in claim 24, wherein said polymerization initiator is selected from the group consisting of peroxide, lauroyl peroxide, benzoyl peroxide and mixtures thereof.

29. The composition as recited in claim 24, wherein said pigment constitutes 0.4–10.0 weight percent of said composition.

30. The composition as recited in claim 24, wherein said pigment constitutes 1.5–15.0 weight percent of said powder component.

31. The composition as recited in claim 24, wherein said pigment has a particle size of less than 5.0 microns.

32. The composition as recited in claim 24, wherein said pigment exhibits a color selected from the group consisting of red, orange yellow, blue, indigo, violet and mixtures thereof.

33. The composition as recited in claim 24, wherein said pigment exhibits a color having a wavelength in the range of 4000–7000 Angstroms.

34. The composition as recited in claim 24, wherein said pigment exhibits a color having a wavelength in the range of 5700–7000 Angstroms.

35. The composition as recited in claim 24, said powder component including a polymerizable acrylic ester monomer.

36. The composition as recited in claim 35, wherein said polymerizable acrylic ester monomer is selected from the group consisting of methylacrylic esters, ethylacrylic esters, butylacrylic esters and mixtures thereof.

37. The composition as recited in claim 35, wherein said alkylmethacrylate polymer and said polymerizable acrylic ester constitute 50–95 weight percent of said powder component.

38. The composition as recited in claim 35, said polymerizable acrylic ester monomer further comprising a polymeric filler dissolved therein.

39. The composition as recited in claim 24, wherein said lower alkylmethacrylate monomer of said liquid component is selected from the group consisting of ethylmethacrylate, butylmethacrylate, propylmethacrylate and mixtures thereof.

40. The composition as recited in claim 24, including an accelerator.

41. The composition as recited in claim 40, wherein said accelerator is a tertiary aromatic amine.

42. The composition as recited in claim 41, wherein said tertiary aromatic amine is selected from the group consisting of N,N-dimethyl-p-toluidine, N,N-diethyl-p-toluidine, N,N-bis(2-hydroxyethyl-p-toluidine) and mixtures thereof.

43. The composition as recited in claim 24, further comprising an additive selected from the group consisting of antioxidants, hardeners, plasticizers, opacifiers, colorant extenders, dispersing agents for pigments and mixtures thereof.

44. The composition as recited in claim 43, wherein said hardener is a calcium compound.

45. The composition as recited in claim 43, wherein said plasticizer is a phthalate ester.

46. The composition as recited in claim 43, wherein said colorant extender is selected from the group consisting of titanium dioxide, alkyl polysiloxane and mixtures thereof.

* * * * *